United States Patent

Laursen

(10) Patent No.: US 7,776,821 B2
(45) Date of Patent: Aug. 17, 2010

(54) METHOD COMPRISING NANOFILTRATION TO OBTAIN AN MBL PRODUCT SAFE FROM INFECTIOUS AGENTS AND THE PRODUCT OBTAINABLE BY THIS METHOD

(75) Inventor: Inga Laursen, Hellerup (DK)

(73) Assignee: Statens Serum Institut (DK)

( * ) Notice: Subject to any disclaimer, the term of this patent is extended or adjusted under 35 U.S.C. 154(b) by 415 days.

(21) Appl. No.: 11/666,034

(22) PCT Filed: Sep. 30, 2005

(86) PCT No.: PCT/DK2005/000621

§ 371 (c)(1),
(2), (4) Date: Apr. 20, 2007

(87) PCT Pub. No.: WO2006/042541

PCT Pub. Date: Apr. 27, 2006

(65) Prior Publication Data

US 2008/0090761 A1 Apr. 17, 2008

(30) Foreign Application Priority Data

Oct. 21, 2004 (DK) ................................ 2004 01616

(51) Int. Cl.
*A61K 38/16* (2006.01)
(52) U.S. Cl. ........................... 514/8; 530/350; 435/69.1
(58) Field of Classification Search ........................ None
See application file for complete search history.

(56) References Cited

U.S. PATENT DOCUMENTS

| 6,429,192 B1 | 8/2002 | Laursen |
| 7,285,646 B2 * | 10/2007 | Bauer ........................ 530/394 |
| 2003/0232969 A1 | 12/2003 | Lengsfel et al. |

FOREIGN PATENT DOCUMENTS

WO   WO 99/64453   12/1999

OTHER PUBLICATIONS

Jensenius et al, Recombinant Mannan-Binding Lectin (MBL) for Therapy, Biochemical Society, vol. 31, Part 4, pp. 763-767, (2003).
Kilpatrick et al, Introduction to Mannan-Binding Lectin, Biochemical Society, vol. 31, Part 4, pp. 745-747, (2003).
Laursen I, Mannan-Binding Lectin (MBL) Production from Human Plasma, Biochemical Society, vol. 31, Part 4, (2003).
Valdimarsson et al, Reconstitution of Opsonizing Activity by Infusion of Mannan-Binding Lectin (MBL) to MBL-Deficient Humans, Scand. J. Immunol. 48, pp. 116-123, (1998).
Burnouf et al, Nanofiltration of Plasma-Derived Biopharmaceutical Products, Haemophilia, vol. 9, No. 1, pp. 24-37, (Jan. 2003).
Miller M., A Familial, Plasma-Associated Defect of Phagocytosis, A New Cause of Recurrent Bacterial Infections, The Lancet, pp. 60-63, (Jul. 13, 1968).
Soothill et al, Defective Opsonization, Archives of Disease in Childhood, vol. 51, pp. 91-99, (1976).
Summerfield et al, Mannose Binding Protein Gene Mutations Associated with Unusual and Severe Infections in Adults, The Lancet, vol. 345, pp. 886-889, (Apr. 8, 1995).
Schwaeble et al, The Mannan-Binding Lectin-Associated Serine Proteases (MASPs) and Map19: Four Components of the Lectin Pathway Activation Complex Encoded by Two Genes, Immunobiology, vol. 205, pp. 455-466, (2002).
Tateishi et al, Scrapie Removal Using Planova Virus Removal Filters, Biologicals, vol. 29, pp. 17-25, (2001).
Turner M.W., Mannose-Binding Lectin: The Pluripotent Molecule of the Innate Immune System, Immunology Today, vol. 17, No. 11, pp. 532-540, (Nov. 1996).
Wallis et al, Structural and Functional Aspects of Complement Activation by Mannan-Binding Protein, Immunology, vol. 205, pp. 433-445, (2002).
I. Laursen et al, "Second generation nanofiltered plasma-derived mannan-binding lectin product: process and characteristics", Vox Sanguinis (2007), published on-line Mar. 2, 2007, vol. 92: 338-350.

* cited by examiner

*Primary Examiner*—Anand U Desai
(74) *Attorney, Agent, or Firm*—Howson & Howson LLP

(57) ABSTRACT

The present nanofiltration method is applicable on solutions of plasma-derived and recombinantly produced MBL. The MBL containing solution is subjected to a pre-treatment prior to the nanofiltration step. The nanofiltration is used for removal of viruses in general and other infectious agents to obtain an MBL product free from infectious viruses and agents. The nanofiltered MBL product is ready for preparing a pharmaceutical composition for therapeutic or prophylactic treatment of infections and other diseases in individuals with MBL deficiency and insufficiency.

24 Claims, 1 Drawing Sheet

METHOD COMPRISING NANOFILTRATION TO OBTAIN AN MBL PRODUCT SAFE FROM INFECTIOUS AGENTS AND THE PRODUCT OBTAINABLE BY THIS METHOD

CROSS-REFERENCE TO RELATED APPLICATIONS

This is a national stage application under 35 U.S.C. 371 of PCT/DK2005/000621, filed on Sep. 30, 2005.

FIELD OF INVENTION

The present invention discloses the use of nanofiltration in the production process of MBL in general for the removal of viruses and other infectious agents such as prions. The invention also discloses an MBL product obtainable by nanofiltration for therapeutic or prophylactic use from which viruses in general and other small size infectious agents or particles such as prions have been removed by the nanofiltration. The pharmaceutical composition prepared from the MBL obtainable by the disclosed method can be used for treatment or prophylaxis of infections or other diseases in individuals with MBL deficiency or insufficiency.

INTRODUCTION

After the outbreak of AIDS in the mid 1980s it was realised that HIV and other blood-borne viruses can be transmitted with blood plasma and plasma products. It has therefore become utmost important in the plasma industry to implement virus reduction steps i.e. virus inactivation and virus removal steps in the production of plasma products. After the recent observation that prions, the infectious agent of variant Creutzfeldt-Jakob disease (vCJD) can be transmitted by plasma, means also have to be taken to minimize such risk by reduction of this agent.

Chemical and physical virus reduction, e.g. S/D treatment and heat treatment are widely used and accepted as important virus reduction steps which effectively inactivate enveloped viruses such as HBV, HCV, and HIV, and also some non-enveloped viruses. More robust non-enveloped viruses such as HAV and parvovirus B19 show resistance to chemical and heat treatment, and additionally have a small size. An extra virus reduction i.e. virus removal step is therefore desired as a precaution to obtain viral safety.

Nanofiltration as a virus removal technique has been implemented in large scale plasma product manufacturing since the early '90s. In the beginning the nanofiltration process was applied in the production of proteins with a MW around 60 kDa, e.g. coagulation factor IX. Today, the technology is also used for larger MW products like immunoglobulins, protease inhibitors, and Factor VIII (Burnouf and Radosevich, 2003).

Mannan-binding lectin (MBL) is a complex protein which is believed to be an important component of the innate immune defence and influencing various diseases (Jensenius et al, 2003). The monomeric MBL-gene product is a 24 kDa polypeptide (Kilpatrick, 2003). Three monomers combine to form one MBL subunit, such subunits further assemble to oligomers. MBL circulates in complex with MBL-associated serine proteases (MASPs) of which there are three types: MASP-1 (90 kDa), MASP-2 (74 kDa) and MASP-3 (94 kDa) (Wallis, 2002; Schwaeble et al, 2002). Active MBL comprises tri- and tetramers and even higher oligomers of the MBL subunits (FIG. 1). The larger the oligomers the more MASPs are bound; the higher the oligomeric form the greater the ability to strongly bind to target surfaces and activate the complement system resulting in elimination of the pathogenic microorganism. To obtain biological activity in a purified MBL preparation it is therefore important to maintain a high degree of oligomeric MBL forms with as many MASPs as possible complexed hereto.

The size of a representative active MBL/MASP complex comprising a tetramer of MBL has a molecular weight around 600-700 kDa. For such a high MW component nanofiltration by filters with narrow pore sizes i.e. 15 nm to 20 nm has until now been reckoned as unsuitable for virus removal without removing MASPs from the complexes with loss of functional activity and/or a high loss of product recovery, especially high MW oligomeric forms.

In WO9837086 nanofiltration of various blood plasma products in particular prothrombin complex concentrate (PCC) is disclosed, but not considered at all in connection with MBL production, probably due to the size of MBL. Actually the plasma protein solution is here pre-treated by tangential flow membrane filtration with cut-off values of 100 to 250 kDa for removal of large contaminating proteins with molecular weights between 400-20.000 kDa to make the subsequent nano-filtration of smaller proteins possible.

Therapy with plasma-derived MBL appears promising for several patient groups and a virus safe production of MBL from plasma is therefore crucial.

MBL deficiency was first clinically manifested by frequent and severe infections in children by an unexplained immune defect (Miller, 1968; Soothill & Harvey, 1976) and was diagnosed as a plasma-associated defect to opsonize yeast, i.e. an inability of the leucocytes to ingest pathogenic microorganisms resulting in infections. Initially this unexplained immune defect was observed in children, especially children up to 18 months of age having an immature immune system. Later on, MBL deficiency as the only immune defect has also been shown to predispose to infections in older children and adults as well.

In four adult patients (15 to 41 years) with severe and unusual infections the only cause of immunodeficiency was mutations in the MBL gene resulting in MBL deficiency (Summerfield et al, 1995). In the first study with intravenous treatment of plasma-derived MBL, a 2-year-old patient and an adult volunteer were treated (Valdimarsson et al, 1998). The adult volunteer was diagnosed as being MBL deficient with all other immunological parameters being normal. This adult volunteer suffered from Psoriasis, chronic fatigue, headaches and irritable bowel symptoms associated with intake of yeast. According to the clinical reports total or partial lack of functional MBL (i.e. MBL deficiency or insufficiency) on its own constitutes a life-long risk to recurrent and severe infections.

Therapeutic grade MBL from plasma is produced by a process comprising chromatographic purification steps where an S/D treatment step is incorporated (see WO9964453 for a state of the art review, and Laursen, 2003). Although affinity chromatography in the process has been shown to remove additional $\log_{10}$ of non-enveloped viruses, it is desirable and even a regulatory demand in processes for plasma products to incorporate an extra robust virus removal or inactivation step especially aiming at small, robust non-enveloped viruses; but also a step to complement the S/D treatment, i.e. an extra safety step removing the enveloped viruses as well. (CPMP/BWP/269/95, rev. 3.3, London, 25 Jan. 2001; CPMP/BWP/268/95, London, 14 Feb. 1996; Bundesanzeiger No. 84, May 1994).

The present invention discloses that a solution containing high-oligomeric MBL alone or in complex with MASPs surprisingly can be filtered through a nanofilter with a pore size around or down to at least 20 nm without any marked loss of product recovery and retaining its biological activity.

An object of this invention is to provide an effective and gentle method to obtain an MBL product free of infectious viruses and agents.

SUMMARY OF THE INVENTION

The present invention discloses a method for producing an MBL containing solution free of viruses and other infectious agents comprising nanofiltration. A nanofilter with pore size down to about 20 nm can be used without marked loss of functional activity and a high recovery. The nanofiltered MBL product, which can be derived from plasma or recombinantly produced MBL, is ready for preparing a pharmaceutical composition for therapeutic or prophylactic treatment of infections and other diseases in individuals with MBL deficiency and insufficiency.

DETAILED DISCLOSURE OF THE INVENTION

Figure 1:
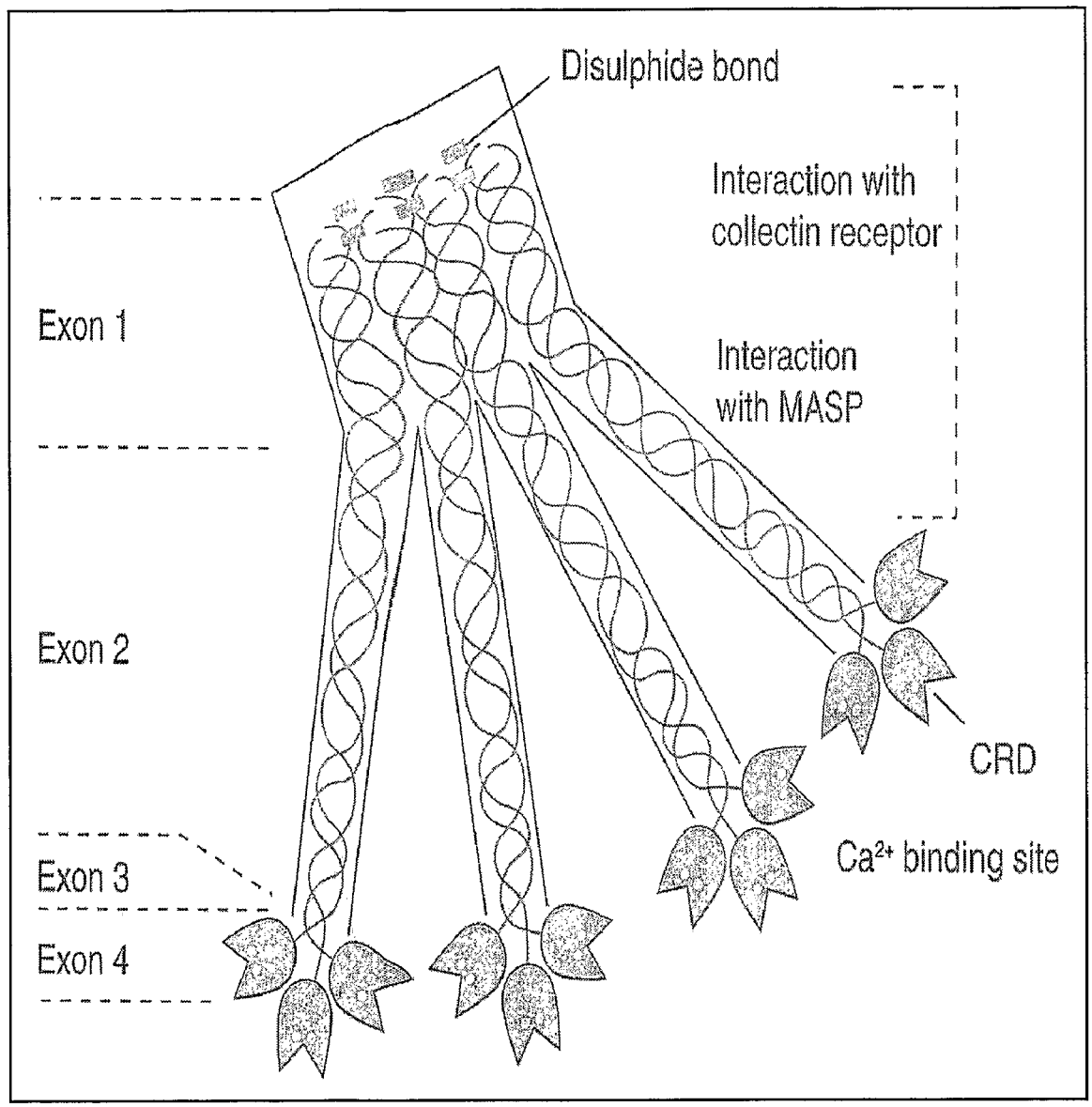
FIG. 1 depicts a model of a tetrameric mannan-binding lectrin (MBL).

The present invention discloses the use of nanofiltration in the production process of MBL in general for the removal of viruses and small infectious agents such as prions.

The method for removing viruses and small infectious agents from an MBL solution can be subjected to a pre-treatment comprising chromatographic purification and/or filtration methods.

The preferred filter for nanofiltration is 15 to 35 nm with the most preferred pore size around 20 nm. The most preferred nanofilter is a Planova 20N® filter (Asahi Kasei, Japan), with a mean pore size of 19 nm.

The present invention also discloses nanofiltration performed as serial filtrations employing 35 nm and/or 20 nm filters.

Furthermore the present invention discloses an MBL product for therapeutic or prophylactic use from which viruses in general and other small size infectious agents or particles such as prions have been removed by nanofiltration.

The present invention also discloses the use of an MBL product which has been nanofiltered for preparing a pharmaceutical composition for therapeutic or prophylactic treatment of infections and other diseases in individuals with MBL deficiency or insufficiency.

The MBL containing solution can be a solution containing recombinantly produced MBL or MBL purified from blood plasma.

The recombinantly produced MBL can be obtained from any suitable expression system. The expression system is preferably a eukaryotic expression system including mammalian cell lines, insect cell lines, yeasts, fungi, or may also be a prokaryotic system, a transgenic animal or a transgenic plant.

The MBL containing solution is preferably a plasma-derived protein solution but can also be a solution containing recombinant MBL with or without MASPs associated. The size of the MBL complex will in general decrease when few or no MASPs associate and also with a lower degree of oligomerisation of MBL subunits. Such relative low MW forms of MBL and MASP-MBL complexes may be filtered through nanofilters with lower pore sizes e.g. from 15 nm to 19 nm without marked loss of recovery The solution constituting the MBL preparation is subjected to an appropriate pre-treatment for removal of undesirable protein contaminants and to prevent clogging of the nanofilter (e.g. by precipitation, column chromatography based on any known kind of separation principle and other well known protein separation technologies). Other virus reducing steps i.e. inactivation and/or removal can also be applied prior to or after the nanofiltration step.

Separation of MBL from other proteins and aggregates during the pre-treatment can be performed as filtrations, which can include membrane and depth filtration (having cut-off values from 0.1 µm to 10 µm), ultrafiltration and diafiltration (cut-off values of 10 to 300 kDa), and also nanofiltration (having pore sizes from 35 to 75 nm).

Chromatographic purification steps can be chosen among affinity chromatographic methods, ion-exchange column chromatography or batch wise separation, gelfiltration (size exclusion chromatography) or any other state of the art chromatographic methods or combinations hereof constituting a process step. MBL can be harvested in the flow through material or the fraction eluted from the column matrix of choice The invention also discloses nanofiltration of a macromolecule, an oligomeric protein and/or a protein complex with a MW of at least 400 kDa through a nanofilter with a pore size down to 20 nm without marked loss of functional activity and a high recovery, and thereby a method for producing a pharmaceutical preparation free from infectious viruses and agents.

Conventionally, virus-removing and -inactivating steps are obligatory in producing plasma proteins for therapeutic use and also recombinantly produced proteins, especially when produced in mammalian cell lines (CPMP/ICH/295/95). The most common virus reduction steps are S/D treatment (e.g. TNBP and Tween 80), heat treatment but also ultra violet radiation, low pH, and enzyme treatment has been used. Such treatments are fairly effective in inactivating enveloped viruses such as HBV, HCV and HIV and some non-enveloped viruses of medium and low resistance. The problematic viruses are robust non-enveloped viruses e.g. HAV (size 25-30 nm) and parvovirus B19 (size 18-24 nm) which are blood-borne, and animal viruses e.g. retroviruses as MLV or SV 40 (size 40-50 nm) contaminating expression systems for recombinant proteins; in addition also new and yet unknown human and/or animal viruses and infectious agents. For both manufacturing of plasma-derived products and recombinant products there is a regulatory demand to show by validation studies employing the infectious viruses or relevant model viruses that specified process steps remove or inactivate the employed virus by a certain reduction factor, i.e. at least 4 $\log_{10}$ for plasma-derived products.

The infectious agent for vCJD constitutes a new problem in both plasma-derived and recombinant products, and specific process steps e.g. precipitation and filtration especially depth filtration and nanofiltration have been shown markedly to reduce the risk of transmission (Tateishi et al, 2001).

The basic principle in virus reduction or reduction of any infectious agents by nanofiltration is removal of such viruses and infectious agents by retainment on a filter based on size, and recovering the protein of interest in the filtrate. This means a technique based on a sieving mechanism not discriminating between enveloped and non-enveloped viruses, robust or non-robust viruses, prion particles or any other infectious agent. In general two filtration methods are possible: cross-flow tangential filtration and flow-through i.e. dead-end filtration. Examples of both methods known in the art of nanofiltration follow.

In addition to variation in pore size, nanofilters are available with different membrane areas e.g. 0.001 $m^2$ to 4 $m^2$, dependent on the amount of protein material to be loaded; and filtration through the various membranes can be operated by different pressures e.g. 0.1 to 5 bar, and at various flow rates dependent on filter-type, -area, and protein concentration of the applied material.

The following are at present the most common brands in nanofilters:

Viresolve® filters (Millipore Corporation) for tangential cross-flow has a cut-off limit of max. 180 kDa, and therefore cannot be used to filter proteins with a higher MW such as oligomeric MBL complexes.

Viresolve® NVP and NVR filters (PVDF membrane) (Millipore) for flow-through filtration are made for retaining parvovirus (applicable for proteins up to 160 kDa) and retrovirus with a size of 80-120 nm, respectively. The latter is not suitable for plasma products as plasma-borne enveloped and non-enveloped viruses with a size <80 nm are not removed.

Ultipor® VF (Pall Life sciences) DV20 and DV50 are hydrophilic modified PVDF microporous pleated membranes for flow-through filtration to retain virus larger than 20 nm and 50 nm, respectively.

Planova® filters (Asahi Kasei Pharma) are hollow fibre microporous membranes made of hydrophilic cuprammonium regenerated cellulose, housed in polycarbonate bodies. They come in various sizes 15N (15 nm+/−2), 20N (19 nm+/−2), 35N (35 nm+/−2), and 75N (72+/−4 nm), where it especially is the 15N and 20N filters that are suited for removing small viruses and especially the non-enveloped such as parvovirus B19 and HAV.

The MBL containing solution can be a solution containing recombinantly produced MBL or MBL purified from blood plasma.

The recombinant MBL may be produced using a variety of expression vectors in various suitable expression systems known in the art. The expression system is preferably a eukaryotic expression system including mammalian cell lines (e.g. BHK cells, CHO cells, HeLa cells or any other mammalian cell line), insect cell lines (e.g. S6 cells), yeasts (e.g. *S. cerevisiae, Sc. pombe, Pichia pastoris*), fungi, or may be a prokaryotic system (e.g. *E. coli, B. subtilis, B. megatherium, L. lactis*). The recombinantly produced MBL is obtained from the expression system as a supernatant, a precipitate or a cell extract. The recombinant MBL may also be obtained from a transgenic animal (e.g. sheep, rabbit, cow, goat, dog, mouse, rat, guinea pig, etc) in the form of a fluid (e.g. milk) or tissue extract, or from a trans-genic plant (e.g. maize, tobacco, wheat, or any other suitable species).

A preferred embodiment of the invention is a purification method of MBL from plasma using ethanol precipitation and affinity chromatography (e.g. as described in WO9964453) followed by an S/D treatment, and for obtaining higher purity subsequently anion-exchange chromatography and gelfiltration. A nanofiltration step can be inserted at several levels in the purification process. Prior to the nano-filtration an optional pre-filtration by a micro- or even a nanofilter can be performed, either as a cross-flow filtration (tangential filtration) or a flow-through filtration (dead-end filtration). Preferred filters for prefiltration are membranes with pore size values from 35 nm to 0.2 μm, such as 75 nm to 0.1 μm, preferably a 0.1 μm filter e.g. Fluorodyne II from Pall. Nanofiltration can be performed as single filtrations or serial filtrations. By serial filtration is meant several single filtrations performed in series or filtration performed by serially connected filters eventually in a parallel way. Serial filtrations can be performed either with more filters of decreasing pore size values or with more filters of the same pore size. By this nanofiltration can be carried out as several concomitant steps or as a single step with one filter or several filters in series, this can also include the prefilter, whatever suits the production process best.

Virus removal is preferably performed with Planova nanofilters 35N or/and 20N, most preferably Planova 20N. The MBL solution for pre- and nanofiltration is taken from a step in the production process. This step can be after the affinity chromatography, which means the eluted fraction from the affinity column; this step can also be after the anion-exchange chromatography, i.e. the eluted fraction from the column; this step can also be before the gelfiltration chromatography, i.e. the fraction concentrated by ultrafiltration; this step can also be after the gelfiltration, i.e. the MBL containing flow-through fraction before formulation as a pharmaceutical composition.

Preferably the eluted fraction from the affinity or the anion-exchange column is chosen for nanofiltration, most preferably the eluted fraction from the affinity column is nanofiltered. As to the conditions for the nanofiltration, the MBL concentration of the solution for nanofiltration is between 10 μg/ml to 10 mg/ml, such as 30 μg/ml to 1 mg/ml, preferably 45 to 200 μg/ml. The purity of MBL is between 40% to 100%, such as 50% to 75%. The temperature of the nanofiltration is between 5° C. to 25° C., optionally room temperature about 20° C. The pressure of the nanofiltration is between 0.2 to 1 bar, such as 0.4 to 0.9 bar, optionally between 0.5 to 0.8 bar. The time of the nanofiltration is between 1 to 17 hrs, such as 2 to 10 hrs, preferably between 3 and 8 hrs. The amount of MBL to be loaded on the nanofilter membrane ranges from 2 to 50 $g/m^2$, such as 3 to 20 $g/m^2$. The recovery from the nanofiltration is between 75% to 100% of the loaded material, such as 85% to 95%. The biological activity of the nanofiltered MBL preparation is fully retained.

The MBL product thus manufactured with an additional virus-reducing step by nanofiltration is considered free of enveloped and non-enveloped viruses and by this virus safe. Furthermore presently unknown as well as new small infectious agents such as prions may also have been removed from the MBL product.

The preferred embodiment of the invention comprises the following steps:

1. solubilisation of an MBL containing plasma fraction harvested after ethanol fractionation and depth filtration or centrifugation;
2. application of the MBL containing solution on a non-conjugated cross-linked polysaccharide material and performing an affinity purification step with desorption of MBL by e.g. mannose or EDTA;
3. performing an S/D treatment step;
4. performing an anion-exchange step with desorption of MBL by NaCl or low pH;
5. concentrating the fraction eluted in step 4 by ultrafiltration;
6. performing a gelfiltration step with collection of an MBL containing flow-through fraction;
7. performing a prefiltration and a nanofiltration between step 2 and 3, or between step 4 and 5, or between step 5 and 6, or after step 6.

The most preferred embodiment of the invention comprises the following steps:

1. solubilisation of an MBL containing plasma fraction harvested after ethanol fractionation and depth filtration;

2. application of the MBL containing solution on a non-conjugated cross-linked polysaccharide matrix and performing an affinity purification step with elution of MBL by mannose;
3. performing a prefiltration and a nanofiltration step;
4. performing an S/D treatment step;
5. performing an anion-exchange step with desorption of MBL by NaCl;
6. concentrating the fraction eluted in step 5 by ultrafiltration;
7. performing a gelfiltration with collection of an MBL containing flow-through fraction;

The MBL product obtainable by the above mentioned production methods can be used to prepare and manufacture a new pharmaceutical composition safe from virus and other infectious agents. This pharmaceutical composition can be used to treat or prevent infections and other diseases in individuals with inherited, congenital or acquired MBL deficiency and insufficiency. The indication for the MBL product is congenital and acquired MBL deficiency/insufficiency, and in particular the MBL product can be used within the following fields:

Neurologic diseases including: chronic inflammatory demyelinating polyneuropathy (CIDP), Multifocal motoric neuropathy, Multiple sclerosis, Myasthenia Gravis, Eaton-Lambert's syndrome, Guillan-Barre's syndrome, Opticus neuritis, Epilepsy, cancer, Gynaecologic diseases including: Abortus habitualis, Primary antiphospholipid syndrome, vaginitis, Rheumatologic diseases including: Rheumatoid arthritis, Systemic lupus erythematosus, Systemic scleroderma, Vasculitis, Wegner's granulomatosis, Sjøgren's syndrome, Juvenile rheumatoid arthritis, Haematologic disorders including: Neutropenia (congenital or acquired, e.g. as a result of medical treatment including chemotherapy), Autoimmune neutropenia, Autoimmune haemolytic anaemia, Gastrointestinal diseases including: Crohn's disease, Colitis ulcerous, Coeliac disease, cancers, Oncologic diseases including: cancers of the stomach, intestine, oesophagus, head, neck, liver, kidney, eye, brain, bone, connective tissue, pancreas, skin, lymph nodes and glands, haemopoietic system, muscle, reproductive tract, and reproductive tissue, Infections including: Bacterial infections (e.g. respiratory tract infections, pneumonia, fascitis, sepsis), fungal infections (e.g. candida vaginitis, aspergillosis), viral infections (e.g. HIV, influenza), parasitic infections (e.g. malaria, trypanosomiasis), Other diseases including: Chronic wounds (e.g. ulcus cruris), Asthma, Septic shock syndrome, Chronic fatigue syndrome, Psoriasis, Toxic shock syndrome, Diabetes I+II, Sinuitis, Dilated cardiomyopathy, Endocarditis, Atherosclerosis, patients with AIDS and bacterial infections, Primary hypo/agammaglobulinaemia including common variable immunodeficiency, Wiskot-Aldrich syndrome and severe combined immunodeficiency (SCID), Secondary hypo/agammaglobulinaemia in patients with cronic lymphatic leukaemia (CLL) and multiple myeloma, Acute and chronic idiopathic thrombocytopenic purpura (ITP), Allogeneic bone marrow transplantation (BMT), Kawasaki's disease.

Used Abbreviations

BVDV, bovine viral diarrhoeal virus (enveloped, size 50-70 nm), model virus for HCV
CPV, canine parvovirus (non-enveloped, size 18-24 nm) model virus for parvovirus B19
ELISA, enzyme-linked immunosorbent assay
HAV, hepatitis A virus (non-enveloped, size 25-30 nm)
HBV, hepatitis B virus (enveloped, size 50 nm)
HCV, hepatitis C virus (enveloped, size 30-45 nm)
HIV, human immunodeficiency virus (enveloped, size 80-100 nm)
MBL, mannan-binding lectin (earlier described as MBP, mannan-binding protein)
MASP, MBL-associated serine proteases. Three types are known: MASP-1, MASP-2 and MASP-3.
MW, molecular weight
S/D treatment, treatment with solvent and detergent
$TCID_{50}$, tissue culture infectious dose 50%

FIG. 1 Depicts a model of a tetrameric MBL (Turner, 1996)

EXAMPLES

Example 1

MBL Extraction and Purification from Plasma

MBL from plasma is purified and virus inactivated according to the procedure disclosed in WO9964453. From a solution of Cohn fractions II+III paste immunoglobulins are recovered by subsequent precipitation of paste II or filtration of the solubilised paste II+III. Non-solubilised MBL is retained in a paste to be harvested from a filter press or a centrifuge i.e. as a fraction III-like paste or paste III precipitated with ethanol. This harvested paste is solubilised and depth filtered, and from this MBL containing solution, MBL is purified by affinity chromatography on a non-conjugated cross-linked polysaccharide matrix e.g. Sepharose CL4B column. The MBL containing eluate fraction from the affinity step is prefiltered and nanofiltered e.g. by use of a 0.1 µm prefilter and two serially connected Planova 20N filters. The nanofiltration is followed by virus inactivation by S/D treatment e.g. 1% Tween 80+0.3% TNBP. The virus inactivated solution is further processed by anion-exchange chromatography e.g. on a Q-Sepharose FF column, and subsequently gelfiltered e.g. on a Superose 6 column. The MBL containing flow-through fraction from the gelfiltration is formulated to constitute the MBL product.

Example 2

Material and Methods for Testing Nanofiltration

MBL Concentration Measurement by ELISA:

The concentration of MBL is determined in an MBL specific sandwich ELISA. A mouse monoclonal antibody is used for catching and also for detection of bound MBL. After binding to the biotinylated secondary antibodies, streptavidin-conjugated HRP converts the colour reagent OPD in a concentration-dependent manner. The concentration of the samples analysed are estimated by use of an MBL plasma standard.

Mannan-binding Activity:

The ligand-binding activity of MBL is determined in an ELISA. Mannan is used for coating of the microtiter plate for subsequent application of the samples. A mouse biotinylated monoclonal antibody against MBL is used for detection of mannan-bound MBL. After binding to the biotinylated antibodies, streptavidin-conjugated HRP converts the colour reagent OPD in a concentration-dependent manner. The mannan-binding activity of the samples analysed are estimated by use of an MBL plasma standard.

C4 Activating Ability:

The C4 activating ability of MBL is determined in an ELISA. Mannan is used for coating of the microtiter plate, for subsequent application of the MBL containing samples. Purified C4 is added to the samples for activation by MASP-2 when in complex with MBL. A biotinylated antibody against C4 is used for detection of bound C4 after activation. After binding to the biotinylated antibodies, streptavidin-conjugated AP converts the colour reagent pNPP in a concentration-dependent manner. The C4 activating ability of the samples analysed are estimated by use of an MBL plasma standard.

Immuno-blotting for Detection of MBL Bands:

Samples drawn before and after the nanofiltration are analysed by SDS-PAGE under non-reducing conditions. Subsequently protein bands from the gel are electro-blotted to a nitrocelluose membrane. The membrane is incubated with monoclonal antibodies against MBL, and subsequently AP-conjugated secondary anti-bodies bind to the MBL-bound antibodies, followed by visualization of the MBL bands by BCIP/NBT.

Example 3

Nanofiltration with DV50 Filter (Load 4.6 g MBL/$m^2$)

A solution of 31 µg/ml MBL in a buffer of 15 mM Tris+0.1 M NaCl+55 mM mannose, pH 7.3, was filtered through a 0.1 µm prefilter with an area of 0.00096 $m^2$ (Fluorodyne II DJLP) and subsequently through a serially connected DV50 filter (Pall FTKDV50) with a membrane area of 0.00096 $m^2$. A volume of 150 ml was loaded on the prefilter and DV50 filter in series, filtration was performed with a pressure of 1 bar, the mean flow was 0.62 ml/min during the filtration; 170 ml of filtrate including washing (washing buffer: 15 mM Tris+0.1 M NaCl+30 mM mannose) was collected.

The nanofiltrate was comparatively analysed with the MBL solution before filtration. No loss was observed for C4 activating ability indicating no MBL-MASPs complexes were destroyed. No loss of mannan-binding activity was measured indicating that no high-oligomeric MBL forms were lost during nanofiltration, which was confirmed by immuno-blotting analysis with use of antibodies to MBL. The recovery of the nanofiltration experiment was 90% of the applied MBL amount.

Example 4

Serial Nanofiltration Through Planova 35N and Planova 20 N Filters (Load 9.3 g MBL/$m^2$), Followed by S/D-treatment and Anion-exchange Chromatography A solution of 55 µg/ml MBL in a buffer of 15 mM Tris+0.1 M NaCl+30 mM mannose, pH 7.3, was prefiltered through a 0.1 µm filter with an area of 0.00096 $m^2$ (Fluorodyne II DJLP), and subsequently through serially connected Planova 35N and Planova 20N filters, both with a membrane area of 0.001 $m^2$. A volume of 170 ml was loaded on the prefilter, filtration was performed with a pressure of 0.1 bar, the flow was 6.1 ml/min, 190 ml of filtrate including washing was collected. The prefiltered MBL solution was applied on the 35 mm filter and 20 nm filters in series, filtration was performed with a mean pressure of 0.8 bar and a mean flow of 0.4 ml/min. The flow decreased from 0.7 to 0.3 ml/min during the filtration. A total of 200 ml nanofiltrate was collected including washing. The nanofiltrate was comparatively analysed with the MBL solution before filtration. No loss was observed for C4 activating ability indicating no MBL-MASPs complexes were destroyed. No loss of mannan-binding activity was measured indicating that no high-oligomeric MBL forms were lost during nanofiltration, which was confirmed by immuno-blotting analysis with use of antibodies to MBL. The recovery of the nanofiltration experiment was 90% of the applied MBL amount.

To study whether the nanofiltration influenced the MBL-MASP complexes during subsequent process steps, the nanofiltrate was added 1% Tween 80+0.3% TNBP and incubated for 6 hrs. at 25° C., for subsequent application on a Q-Sepharose column. The MBL solution eluted from the Q Sepharose column was analysed for C4 activating ability, no loss was observed indicating the MBL-MASPs complexes were not fragile after the nanofiltration.

Example 5

Nanofiltration Through Single Planova 20 N Filter (Load 6.5 g MBL/$m^2$)

A solution of 76 µg/ml MBL in a buffer of 15 mM Tris+0.1 M NaCl+55 mM mannose, pH 7.3 was prefiltered through a 0.1 µm filter with an area of 0.00096 $m^2$ (Fluorodyne II DJLP), and subsequently through a Planova 20N filter with a membrane area of 0.001 $m^2$. A volume of 85 ml was loaded on the prefilter, filtration was performed with a pressure of 0.1 bar, the flow was 3.1 ml/min, 105 ml of filtrate including washing was collected. The prefiltered MBL solution was applied on the 20 nm filter; filtration was performed with a pressure of 0.6 bar and a mean flow of 0.55 ml/min. A total of 113 ml nanofiltrate was collected including washing.

The nanofiltrate was comparatively analysed with the MBL solution before filtration. No loss was observed for C4 activating ability indicating no MBL-MASPs complexes were destroyed. No loss of mannan-binding activity was measured indicating that no high-oligomeric MBL forms were lost during nanofiltration, which was confirmed by immuno-blotting analysis with use of antibodies to MBL. The recovery of the nanofiltration was 89% after Planova 20N of the MBL amount applied after prefiltration.

Example 6

Validation of Virus (CPV) Removal Through Dead-End Single Planova 20N Filtration, Serial Planova 35N and Planova 20N Filtration, and Double Planova 20N Filtration (Load 3.2 g MBL/$m^2$)

These virus removal steps were validated in accordance with the CPMP Note for guidance on Virus Validation Studies (CPMP/BWP/268/95) and Note for Guidance of Plasma Derived Medicinal Products (CPMP/BWP/269/95). The aim of the study was to evaluate the clarification capacity of the nanofiltration (expressed as reduction factor=removal of $\log_{10}$ of virus) of CPV (a model of parvovirus B19) spiked to the material before nanofiltration.

A solution of 46 µg/ml MBL in a buffer of 15 mM Tris+0.1 M NaCl+30 mM mannose, pH 7.3, was prefiltered through a 0.1 µm filter with an area of 0.00096 $m^2$ (Fluorodyne II DJLP). A volume of 208 ml was loaded on the prefilter, filtration was performed with a pressure of 0.1 bar, the flow was 4.5 ml/min, 212 ml of filtrate including washing was collected. A volume of 69 ml of the prefiltered MBL solution was spiked with 0.7 ml CPV inoculate to a titer of $10^{5.65}$ $TCID_{50}$/ml, and 69 ml was applied on a 20 nm filter (area 0.001 m$^2$), filtration was performed with a pressure of 0.65 bar and a mean flow of 0.6 ml/min. A volume of 66.8 ml filtrate was collected in 2 fractions (filtrate 1 of 31.6 ml and filtrate 2 of 35.2 ml), subsequently 26.8 ml of washing (washing buffer: 15 mM Tris+0.1 M NaCl+30 mM mannose) was collected. A volume of 69 ml of the prefiltered MBL solution was spiked with 0.7 ml CPV inoculate to a titer of $10^{5.77}$ $TCID_{50}$/ml, and 69 ml was applied on serially connected Planova 35N and Planova 20N filters (areas 0.001 m$^2$), filtration was performed with a pressure of 0.75 bar and a mean flow of 0.6 ml/min. A volume of 66.8 ml filtrate was collected in 2 fractions (filtrate 1 of 36.8 ml and filtrate 2 of 30 ml), subsequently 20.6 ml of washing was collected. A volume of 69 ml of the prefiltered MBL solution was spiked with 0.7 ml CPV inoculate to a titer of $10^{5.83}$ $TCID_{50}$/ml, and 69 ml was applied on two serially connected Planova 20 N filters (areas 0.001 m$^2$), filtration was performed with a pressure of 0.9 bar and a mean flow of 0.4 ml/min. A volume of 65.8 ml filtrate was collected in 2 fractions (filtrate 1 of 34.5 ml and filtrate 2 of 31.3 ml); subsequently 19 ml of washing was collected.

The virus removing capacity obtained during the 3 validated nanofiltration experiments appears from table 1.

filtrate was collected, subsequently 23.4 ml of washing (washing buffer: 15 mM Tris+0.1 M NaCl+30 mM mannose) was collected. A volume of 130 ml of the prefiltered and virus-spiked MBL solution was applied on two serially connected Planova 35N filters (areas 0.001 m$^2$); filtration was performed with a pressure of 0.5 bar and a mean flow of 0.7 ml/min. A volume of 122.5 ml filtrate was collected; subsequently 44.8 ml of washing was collected.

The virus removing capacity obtaining during the 2 nanofiltration experiments appears from table 2.

TABLE 2

Results of virus validation study after spiking with BVDV expressed by RF (reduction factor) = $\log_{10}$ of virus removed

| Sample | BVDV |
| --- | --- |
| Filtrate, single Planova 35N | >4.9 ± 0.2 & ≦6.0 ± 0.2 |
| Washing, single Planova 35N | ≧4.2 ± 0.2 & ≦6.3 ± 0.2 |
| Filtrate, double Planova 35N | >6.0 ± 0.2 |
| Washing, double Planova 35N | >5.3 ± 0.2 & ≦6.4 ± 0.2 |

TABLE 1

Results of virus validation study after spiking with CPV expressed by RF (reduction factor) = $\log_{10}$ of virus removed

| | RF ($\log_{10}$) of CPV | | |
| --- | --- | --- | --- |
| Sample | Nanofiltration with single Planova 20N | Nanofiltration with serial Planova 35N and 20N | Nanofiltration with double Planova 20N |
| Filtrate 1 | ≧3.5 ± 0.3 & ≦5.6 ± 0.3 | ≧3.6 ± 0.3 & ≦5.7 ± 0.3 | >6.1 ± 0.3 |
| Filtrate 2 | ≧3.4 ± 0.3 & ≦5.6 ± 0.3 | ≧2.9 ± 0.4 & ≦5.7 ± 0.3 | >5.0 ± 0.3 & ≦6.1 ± 0.3 |
| Washing | ≧3.2 ± 0.3 & ≦5.6 ± 0.3 | ≧2.9 ± 0.4 & ≦5.7 ± 0.3 | >5.0 ± 0.3 & ≦5.8 ± 0.3 |

Example 7

Validation of Virus (BVDV) Removal Through Dead-end Single Planova 35N Filtration, and Double Planova 35N Filtration (Load 5.2 and 5.7 g MBL/m$^2$)

These virus removal steps were validated in accordance with the CPMP Note for guidance on Virus Validation Studies (CPMP/BWP/268/95) and Note for Guidance of Plasma Derived Medicinal Products (CPMP/BWP/269/95). The aim of the study was to evaluate the clarification capacity of the nanofiltration (expressed as reduction factor=removal of $\log_{10}$ of virus) of BVDV (a model of HCV) spiked to the material before nanofiltration.

A solution of 49 μg/ml MBL in a buffer of 15 mM Tris+0.1 M NaCl+55 mM mannose, pH 7.3, was prefiltered through a 0.1 μm filter with an area of 0.00096 m$^2$ (Fluorodyne II DJLP). A volume of 370 ml was loaded on the prefilter; filtration was performed with a pressure of 0.2 bar, 354 ml of filtrate was collected without washing. A volume of 250 ml of the prefiltered MBL solution was spiked with 2.5 ml BVDV inoculate to a titer of $10^{5.60}$ $TCID_{50}$/ml. A volume of 107.5 ml virus-spiked MBL solution was applied on one 35 nm filter (area 0.001 m$^2$), filtration was performed with a pressure of 0.5 bar and a mean flow of 1.4 ml/min. A volume of 104.5 ml

REFERENCES

Burnouf, T. and Radosevich, M., Heamophiliae, 2003, 9, 24-37
Jensenius, J. C. et al, Biochemical Society Transactions, 2003, 31(4), 763-767
Kilpatrick, D., Biochemical Society Transactions, 2003, 31(4), 745-747
Laursen, I., Biochemical Society Transactions, 2003, 31(4), 758-762
Miller, M. E., The Lancet, 1968 Jul. 13, 60-63
Soothill, J. F. and Harvey, B. A. M, 1976, 51. 91-99
Summerfield, J. A. et al, The Lancet, 1995, 345, April 8, 886-889
Schwaeble, W. et al, Immunobiology, 2002, 205, 455-466
Tateishi, J. et al, Biologicals, 2001, 29, 17-25
Turner, M. W., Immunology Today, 1996, 17, 532-540.
Valdimarsson, H. et al, Scand. J. Immunol., 1998, 48, 116-123
Wallis, R., Immunobiology, 2002, 205, 433-445

The invention claimed is:

1. A method for removing viruses and small infectious agents from an active form of MBL containing solution comprising nanofiltration of the solution.

2. A method according to claim 1, where the nanofilter pore size is 15-35 nm.

3. The method according to claim 1, where the MBL containing solution has been subjected to a pre-treatment.

4. A method according to claim 3, where the pre-treatment comprises chromatographic purification and/or filtration.

5. A method according to claim 4, where the pre-treatment filtration is membrane and/or ultrafiltration.

6. The method according to claim 1, wherein the MBL containing solution contains recombinantly produced MBL or MBL from blood plasma.

7. A method according to claim 6, where the MBL is produced recombinantly from expression system.

8. A method according to claim 1 where the process comprises the following steps:
  (A) solubilisation of an MBL containing plasma fraction harvested after ethanol fractionation and depth filtration;
  (B) application of the MBL containing solution of step A on a non-conjugated cross-linked polysaccharide material and performing an affinity purification step;
  (C) performing an S/D treatment on the material eluted in step B;
  (D) performing an anion-exchange on the material from step C;
  (E) concentrating the fraction eluted in step D by ultrafiltration;
  (F) performing a gelfiltration on the material from step E;
  (G) performing a prefiltration and nanofiltration between step B and C, or between step D and E, or between step E and F, or after step F.

9. A method according to claim 8 where the prefiltration and nanofiltration are performed between step B and C.

10. The method according to claim 4, where the pre-treatment filtration is dead-end and/or cross-flow tangential filtration.

11. The method according to claim 1, where the nanofiltration is performed with a 35 nm filter.

12. The method according to claim 1, where the nanofiltration is performed with a 20 nm filter.

13. The method according to claim 1 where the nanofiltration is performed as serial filtrations employing 35 nm and/or 20 nm filters.

14. A method according to claim 1, where the conditions for the nanofiltration are as follow: an MBL concentration between 10 µg/ml to 10 mg/ml; a purity of the MBL solution between 40% to 100%, a temperature between 5° C. to 25° C.; a pressure between 0.2 to 1 bar; an MBL loading between 2 g/m$^2$ to 50 g/m$^2$.

15. The method according to claim 1, wherein the small infectious agents are prions.

16. The method according to claim 7, where the expression system is a eukaryotic expression system comprising cells selected from mammalian cell lines, insect cell lines, yeasts and fungi.

17. The method according to claim 7, wherein the expression system is a prokaryotic expression system.

18. The method according to claim 14, wherein the MBL concentration is between 45 to 200 µg/ml.

19. The method according to claim 14, wherein the temperature is about 20° C.

20. The method according to claim 14, wherein the pressure is between 0.5 bar to 0.8 bar.

21. The method according to claim 14, wherein the MBL loading is between 3 g/m$^2$ to 20 g/m$^2$.

22. A method of nanofiltering macromolecule, an oligomeric protein and/or a protein complex with a molecular weight of at least 400 kDa through a nanofilter with a pore size down to 20 nm.

23. A method according to claim 22 for producing a pharmaceutical preparation free from infectious viruses and agents.

24. A method of treating patients with MBL deficiency or insufficiency by delivering a pharmaceutical composition to the patient comprising an MBL product produced according to method of claim 1.

* * * * *